United States Patent [19]

Pegel et al.

[11] Patent Number: 4,929,603
[45] Date of Patent: May 29, 1990

[54] USE OF PHYTOSTERYL GLYCOSIDES FOR THE TREATMENT OF EPOXYCHOLESTEROL LEVELS

[75] Inventors: Karl H. Pegel, Durban, South Africa; Hans Walker, Eschwege, Fed. Rep. of Germany

[73] Assignee: Rooperal (NA) NV, Amsterd AM

[21] Appl. No.: 262,130

[22] Filed: Oct. 25, 1988

Related U.S. Application Data

[63] Continuation of Ser. No. 918,940, Oct. 15, 1986, abandoned, which is a continuation-in-part of Ser. No. 690,607, Jan. 11, 1985, abandoned.

[30] Foreign Application Priority Data

Jan. 14, 1984 [DE] Fed. Rep. of Germany ....... 3401178

[51] Int. Cl.$^5$ .............................................. A61K 31/70
[52] U.S. Cl. ...................................................... 514/26
[58] Field of Search .......................................... 514/26

[56] References Cited

FOREIGN PATENT DOCUMENTS 0007474 2/1980 European Pat. Off. ............. 514/26

OTHER PUBLICATIONS

Sporer et al., *Urology*, 9-1982 No. 3, pp. 244-250.

*Primary Examiner*—Johnnie R. Brown
*Assistant Examiner*—Elli Peselev
*Attorney, Agent, or Firm*—Morgan & Finnegan

[57] ABSTRACT

The invention relates to the use of phytosteryl glycoside or their esters for the treatment of conditions caused by increased endogenous epoxycholesterol levels in human organs and organ fluids especially those with glandular function; and to compositions and method for treating such conditions.

1 Claim, No Drawings

USE OF PHYTOSTERYL GLYCOSIDES FOR THE TREATMENT OF EPOXYCHOLESTEROL LEVELS

This is a continuation of co-pending application Ser. No. 918,940, filed on Oct. 15, 1986 (now abandoned), and U.S. Ser. No 06/690,607 filed Jan. 11, 1985 (now abandoned).

This invention relates to the use of phytosteryl glycosides or their esters for the prevention and treatment of increased endogenous epoxycholesterol levels, in human organs or organ fluids.

The scientific and research interests in cholesterol's function and metabolism in the past was mainly orientated towards the significant role cholesterol may play in the development of atherosclerosis and related disorders. Only very recently has it been established that some metabolites of cholesterol appear to be instrumental in inducing or promoting the formation of neoplastic disorders and possibly other conditions. It has been shown that in normal healthy tissue cholesterol is readily oxidised under the influence of enzymes of 5(6)α-epoxycholesterol and 5(6)β-epoxycholesterol, the latter compound being regularly present in 3-4 fold excess over the α-isomer. It has been shown by Blackburn et al, Chem. Commun., 420–421, 1979; Imai et al, Science 207, 651–653, 1980; Kelsey, Cancer Lett., 6, 143–149, 1979, and Parson et al in Aust. J. Exp. Biol. Med., 56, 287–296, 1978, that the ratio between α-isomer to β-isomer of the epoxycholesterol is completely altered in cancerous or precancerous tissue since an excess of the α-isomer over the β-isomer is present in these in a ratio of 8-12 to 1. 5(6)α-Epoxycholesterol is considered to be a typical carcinogenic—as well as a cytotoxic compound and has been compared by Kelsey et al with the known potent carcinogen 3-methylcholanthrene. The significant mutagenic effect of the two cholesterol epoxides on cell cultures has been described by Sevanian et al in Proc. Natl. Acad. Sci. U.S.A., 81, 4198–4202, 1984.

Both epoxycholesterols are probably normal endogenous metabolites produced in the liver, and probably in many other tissues, during the metabolic transformation from cholesterol to cholestane-3β,α5β,6-triol (see for example C. P. Schaffner in "Benign Prostatic Hypertrophy", Ed. F. Hinman, 1983, Springer, pp 295–302).

Inhibition of the cholesterol metabolic pathway towards cholestanetriol manifests itself by an accumulation of cholesterol and/or its epoxides leading to subsequent epoxycholesterol mediated tissue damage, e.g. hyperplasia in the affected organ or environment. Methods for the reduction or prevention of abnormal and especially epoxycholesterol levels are therefore of therapeutic importance.

For example, in DT-OS 21 13 215, or GB. 12 98 047 sitosteryl glycoside has been suggested for the reduction of plasma cholesterol levels while sitosterol has been used for this purpose over the past 30 years. Many different chemical compounds are used at present for reducing increased plasma cholesterol levels. However, no relevant information is available indicating that they also reduce the epoxycholesterols levels in the body organs or fluids.

In USP 4 461 762 Malinow describes the use of relatively large doses (14 mg single doses per rat approximating to 4.5 g per 80 kg person) of glucosides and cellobiosides of diosgenin and tigogenin for the inhibition of absorption of cholesterol from the intestinal track in the treatment of hypercholesterolemia.

Surprisingly small doses (0,45 mg/day for 6 month—total of 81 mg per person) of sitosteryl glucoside and its related phytosterol glycosides (sterolins) are effective in reducing cholesterol and epoxycholesterol levels in human organs and organ fluids (see Example 2) only after their absorption on oral administration. Radioactively labelled sitosteryl glucosides, orally administered, has been detected in the serum and urine of human volunteers (see Example 3) and is incorporation in mouse, rat and human lipoproteins (J. Skei et al: J. Pharm. Sci., 1985, 74, 1259–1264).

Surprisingly it has now been found that sterolins in small daily doses can reduce or prevent the increase of the epoxycholesterols in human organs and organ fluids. It is expected that this effect proceeds via a regeneration or normalization of the enzyme system which is responsible for the transformation of the epoxides into the triol.

According to the invention it is now proposed that the pharmaceutically-acceptable glucosides, maltosides, mannosides, galactosides, lactosides, arabinosides or cellobiosides of sitosterol, campesterol, stigmasterol, spinasterol or 5α-5,6-diphydrosterols and their esters, with a pharmaceutically-acceptable carrier are used for the treatment of increased endogenous epoxycholesterol levels, and therefore for the prophylactic or therapeutic treatment of benign tissue degeneration.

The above phytosteryl glycosides often designated as sterolins, and their 6'-O-acylesters with fatty acids are naturally occurring compounds which can be synthesized as described for example in DT-OS 27 59 171 or GB 20 39 217.

The hemiesters of dicarboxylic acids can be used as has been described in the European Patent Application 0007474.

The compounds under consideration correspond to the following formula,

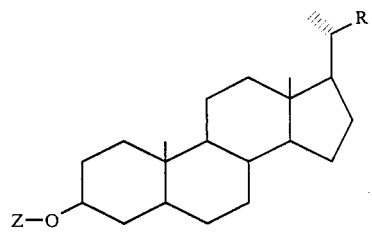

in which Z means a sugar group which can be esterified, R is a side chain with 6 to 8 carbon atoms which can be unsaturated and in the sterane skeleton C-5, if saturated, and C-14 have the α-configuration. Moreover, the sterane skeleton can carry double bonds particularly at C-5 or C7.

The invention is now explained in more detail in the examples.

EXAMPLE 1

The preparation of steryl glycosides proceeds according to the known method of the Königs-Knorr synthesis for the production of glucosides or glycosides using an aglycone alcohol and a C-1 brominated carbohydrate acetate in the presence of silver- or cadmium salts (oxides or carbonates) as catalysts.

Similarly different glycosides of sitosterol can be produced. By choosing different aglycon alcohols other glycosides of phytosterols besides sitosterol can be synthesized as for example those derived from campesterol, stigmasterol, spinasterol, cholesterol or 5,6-dihydrositosterol.

Esters of the glycosides (sterolins) can be prepared by known methods by esterification of the free OH-groups or by trans-esterification of the acetates or as described in European Patent Application 0007474.

EXAMPLE 2

The lowering of epoxycholesterols was determined in prostate 'exprimate' obtained by rectal prostatic gland massage since it is known that epoxycholesterol is present in the human prostate of patients suffering from prostate hyperplasia or prostate carcinoma as had been described in the dissertation of David Reinhold Brill, State University of New Jersey, New Jersey, May 1981.

The measurements were done on exprimates from various men of different ages. In each case the first 'exprimate' sample was taken prior to treatment with phytosteryl glycoside and the second 'exprimate' sample after a six months treatment with sitosteryl glucoside in amounts of 0.45 mg/daily. The epoxycholesterol were identified as the trimethylsilyl ether using GC/NS. Quantitive determination was executed by integration of peak areas using cholesteryl methyl ether as internal standard.

10 μg internal standard were added to 50 μl exprimate in a 5 ml centrifuge tube with a screw-top lid and followed by liophilisation of the mixture. The lyophilized precipitate was vortexed with 2 ml chloroform/methanol 2:1 and treated ultrasonically, centrifuged for 5 minutes at 2000 rpm and the supernatant transferred into a second tube. The extraction was repeated twice and the combined extracts washed with 1 ml physiological sodium chloride solution discarding the aqueous phase. The organic phase was dried over sodium sulphate and evaporated to dryness under a stream of nitrogen at 50° C. on a sandbath. A volume of 1 ml silylizing reagent was added to the residue, the reagent consisting of 5 ml dry pyridine, 3 ml hexanmethyldisilazane and 1 ml chlortrimethylsilane. The reaction mixture was kept on a sandbath at 60° C. for 1 hour and dried under a stream of nitrogen, followed by treatment with 0.5 ml hexane and ultrasonically dispersed and then centrifuged at 2000 rpm. The supernatant was transferred into a vial, and reduced to a final volume of 30 μl.

Mixtures, containing the 3 components in increasing amount in the following concentrations were prepared for the standard curve:

| | |
|---|---|
| Cholesterol | 0–75 μg/50 μl |
| Cholesterolepoxide | 0–3 μg/50 μl |
| Cholesteryl methyl ether constant | 0–10 μg/50 μl |

These standards were treated in the same manner as the samples.

| | |
|---|---|
| Gaschromatographic conditions | |
| Instrument | Carlo Erba Fracto vap 4160 |
| Carrier gas | hydrogen, 09 bar initial pressure |
| Separating capillary | 25 m glas, 035 μm SE 52 |
| Temperature programme | 180° C. (3 minutes) - 10° C./min. - 280° C. (30 minutes) |
| Injection | 2 μl on column at 40° C. |
| Masspectrometric conditions | |
| Spectrograph employed | MS 30 computerized, by Kratos |
| Ionisation | at 70 eV, EI |
| Scanspeed | 6 sec/spectrum |
| Mass region | 30–650 m/e |

The evaluation of the epoxycholesterol concentration in μg/ml of prostate exprimates showed that with an initial small amount between about 5–10 μg/ml a decrease to 0 in the second sample after 6 months had occurred. Particularly surprising, however, was the reduction of initially high values in that measurements showed a decrease from 59 μg/ml to 6, from 109 to 67 and from 111 to 0 μg/ml.

TABLE

| PATIENT | CHOLESTEROL-EPOXIDE μg/ml | | CHOLESTEROL μg/ml | |
|---|---|---|---|---|
| | 1st DETERMINATION | 2nd DETERMINATION | 1st DETERMINATION | 2nd DETERMINATION |
| 1. O. S. | 109 | 67 | 4.0 | 0.63 |
| 2. J. S. | 59 | 6 | 9.0 | 1.0 |
| 3. K. B. | 5 | 0 | 7.1 | (not done) |
| 4. G. S. | 6 | 0 | 9.6 | 0.6 |
| 5. K. S. | 3 | 0* | 1.6 | 1.44 |
| 6. W. | 11 | 0* | 4.5 | 0.48 |
| 7. A. G. | 11 | 7 | 4.9 | 0.42 |
| 8. B. I. | 111 | 0 | 6.4 | 0.58 |

*At Determination Limit

EXAMPLE 3

Radioactively labelled sitosteryl glucoside (4-$^{14}$C), administered orally to two male volunteers, was detected in the serum, urine and faeces as shown in Tables 1, 2 and 3 below. In these tables "WA 184" refers to sitosteryl glucoside.

Metabolic fate of $^{14}$C-WA 184 in human subjects after oral doses

Centre: The Institute of Clinical Pharmacology, St. James' Hospital, Dublin and the Department of Metabolism and Pharmacokinetics, Huntingdon Research Centre.

$^{14}$C-WA 184 on lactose, 1:100 w/w weighed into gelatin capsules.

2 male subjects entered the study. Each received 3 mg WA 184 (containing 50 μCl $^{14}$C) i.e. 300 mg of WA 184 lactose mixture, contained in 2 gelatin capsules.

TABLE 1

Concentrations of radioactivity in plasma after single oral doses of 4-$^{14}$C-WA 184 (3 mg) to two male human volunteers. Formulation used was $^{14}$C-WA 184/lactose (1:99, w/w) Results are expressed as ng equivalent to WA 184/ml

| Time (hours) | Subject | |
|---|---|---|
| | 1 (M.T.) | 2 (K.G.) |
| predose | ND | ND |
| 0.5 | 8.5 | 4.4 |
| 1 | 19.1 | 14.1 |
| 1.5 | 21.2 | 15.3 |
| 2 | 18.3 | 18.1 |
| 3 | 19.5 | 17.4 |
| 4 | 19.0 | 17.7 |
| 5 | 20.1 | 19.8 |
| 6 | 22.2 | 21.2 |
| 8 | 21.2 | 21.4 |

TABLE 1-continued

Concentrations of radioactivity in plasma after single oral doses of 4-$^{14}$C-WA 184 (3 mg) to two male human volunteers. Formulation used was $^{14}$C-WA 184/lactose (1:99, w/w) Results are expressed as ng equivalent to WA 184/ml

| Time (hours) | Subject 1 (M.T.) | Subject 2 (K.G.) |
|---|---|---|
| 10 | 17.7 | 19.6 |
| 12 | 15.1 | 18.1 |
| 16 | 14.4 | 14.2 |
| 24 | 12.9 | 13.3 |
| 32 | 12.2 | 14.3 |
| 48 | 10.2 | 10.7 |
| 72 | 7.1 | 8.8 |
| 96 | 6.6 | 7.1 |
| 120 | 6.0 | 6.6 |

ND = below the level of accurate determination (1.4 ng equiv/ml)

TABLE 2

Excretion of radioactivity in urine after single oral doses of 4-$^{14}$C-WA 184 (3 mg) to two male human volunteers. Formulation used was $^{14}$C-WA 184/lactose (1:99, w/w).

| Time interval (hours) | Subject 1 (M.T.) | | Subject 2 (K.G.) | |
|---|---|---|---|---|
| | % dose | Cumulative % dose | % dose | Cumulative % dose |
| predose | ND | — | ND | — |
| 0-2 | 1.13 | 1.13 | 0.75 | 0.75 |
| 2-4 | 0.75 | 1.88 | 0.72 | 1.47 |
| 4-6 | 1.10 | 2.98 | 0.90 | 2.37 |
| 6-8 | 0.83 | 3.81 | 0.63 | 3.00 |
| 8-10 | 0.54 | 4.35 | 0.57 | 3.57 |
| 10-12 | 0.55 | 4.90 | 0.36 | 3.93 |
| 12-24 | 0.91 | 5.81 | 0.79 | 4.72 |
| 24-48 | 0.95 | 6.76 | 0.96 | 5.68 |
| 48-72 | 0.22 | 6.98 | 0.46 | 6.14 |
| 72-96 | 0.10 | 7.08 | 0.15 | 6.29 |
| 96-120 | 0.05 | 7.13 | 0.09 | 6.38 |

TABLE 3

Excretion of radioactivity following single oral doses of 4-$^{14}$C-WA 184 (3 mg) to two male volunteers. Results are expressed as % dose administered

| Time interval (hours) | Subject 1 (M. T.) | | Subject 2 (K. G.) | |
|---|---|---|---|---|
| | Urine | Faeces | Urine | Faeces |
| 0-24 | 5.81 | 50.55 | 4.72 | 2.81 |
| 24-48 | 0.95 | 22.95 | 0.96 | 31.74 |
| 48-72 | 0.22 | 12.22 | 0.46 | 38.03 |
| 72-96 | 0.10 | 2.63 | 0.15 | 10.81 |
| 96-120 | 0.05 | 1.37 | 0.09 | 4.57 |
| Total | 7.13 | 89.72 | 6.38 | 87.96 |
| Total recovery | 96.85 | | 94.34 | |

We claim:

1. The method of treatment of increased endogenous 5(6)α-epoxycholesterol level in the prostate gland of a human comprising providing a daily administration of a dose as small as 0.45 mg of β-sitosterol glucoside.

* * * * *